United States Patent
Verner

(10) Patent No.: US 12,102,406 B2
(45) Date of Patent: Oct. 1, 2024

(54) SYSTEM AND METHOD FOR REPOSITIONING INPUT CONTROL DEVICES

(71) Applicant: INTUITIVE SURGICAL OPERATIONS, INC., Sunnyvale, CA (US)

(72) Inventor: Lawton N. Verner, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 14 days.

(21) Appl. No.: 16/758,832

(22) PCT Filed: Oct. 22, 2018

(86) PCT No.: PCT/US2018/056874
§ 371 (c)(1),
(2) Date: Apr. 23, 2020

(87) PCT Pub. No.: WO2019/083886
PCT Pub. Date: May 2, 2019

(65) Prior Publication Data
US 2021/0030502 A1    Feb. 4, 2021

Related U.S. Application Data

(60) Provisional application No. 62/577,020, filed on Oct. 25, 2017.

(51) Int. Cl.
*A61B 34/00* (2016.01)
*A61B 90/00* (2016.01)
*G16H 40/63* (2018.01)

(52) U.S. Cl.
CPC ............. *A61B 34/74* (2016.02); *A61B 90/06* (2016.02); *G16H 40/63* (2018.01); *A61B 2090/061* (2016.02); *A61B 2090/065* (2016.02)

(58) Field of Classification Search
CPC ... A61B 34/74; A61B 90/06; A61B 2090/061; A61B 2090/065; A61B 34/37; A61B 34/35; G16H 40/63; B25J 13/02
See application file for complete search history.

(56) References Cited

U.S. PATENT DOCUMENTS

| | | | |
|---|---|---|---|
| 5,390,288 | A | 2/1995 | Toda et al. |
| 5,817,084 | A | 10/1998 | Jensen et al. |

(Continued)

FOREIGN PATENT DOCUMENTS

| | | | | |
|---|---|---|---|---|
| EP | 2480158 B1 | * | 5/2016 | ............ A61B 34/30 |
| EP | 3119323 A1 | | 1/2017 | |

(Continued)

OTHER PUBLICATIONS

Hybrid tracking of human operators using IMU/UWB data fusion by a Kalman Filter, Corrales et al, HRI'08, Mar. 12-15, 2008, Amsterdam, Netherlands, 2008 ACM 978-1-60558-017; see attached NPL (Year: 2008).*

(Continued)

*Primary Examiner* — Gary Jackson
*Assistant Examiner* — Ranjani Mari Sundaresan
(74) *Attorney, Agent, or Firm* — Artegis Law Group, LLP

(57) ABSTRACT

A system and method of repositioning input control devices includes an operator workstation for controlling a computer-assisted device includes an input control device for use by an operator, one or more sensors, and a controller coupled to the one or more sensors and the input control device. The controller is configured to determine whether the operator is interacting with the input control device using the one or more sensors and in response to determining a lack of operator interaction with the input control device, determine a trajectory for moving the input control device from a current position or orientation toward a desired position or (Continued)

orientation, and move the input control device along the trajectory. In some embodiments, the controller is further configured to stop movement of the input control device along the trajectory in response to detecting a stopping condition.

27 Claims, 3 Drawing Sheets

(56) References Cited

U.S. PATENT DOCUMENTS

| | | | |
|---|---|---|---|
| 6,468,265 B1 | 10/2002 | Evans et al. | |
| 8,004,229 B2 | 8/2011 | Nowlin et al. | |
| 8,189,738 B2 | 5/2012 | Dussault et al. | |
| 8,332,072 B1 | 12/2012 | Schaible et al. | |
| 8,541,970 B2 | 9/2013 | Nowlin et al. | |
| 8,620,473 B2 | 12/2013 | Diolaiti et al. | |
| 8,624,537 B2 | 1/2014 | Nowlin et al. | |
| 8,681,098 B2 * | 3/2014 | Underkoffler | G06F 18/285 |
| | | | 345/158 |
| 8,749,189 B2 | 6/2014 | Nowlin et al. | |
| 8,749,190 B2 | 6/2014 | Nowlin et al. | |
| 8,786,241 B2 | 7/2014 | Nowlin et al. | |
| 8,816,628 B2 | 8/2014 | Nowlin et al. | |
| 8,823,308 B2 | 9/2014 | Nowlin et al. | |
| 9,066,737 B2 | 6/2015 | Bärwinkel et al. | |
| 9,084,623 B2 | 7/2015 | Gomez et al. | |
| 9,138,129 B2 | 9/2015 | Diolaiti | |
| 9,333,042 B2 | 5/2016 | Diolaiti et al. | |
| 9,469,034 B2 | 10/2016 | Diolaiti et al. | |
| 9,516,996 B2 | 12/2016 | Diolaiti et al. | |
| 9,717,563 B2 | 8/2017 | Tognaccini et al. | |
| 9,774,827 B2 | 9/2017 | Tanaka et al. | |
| 10,258,425 B2 | 4/2019 | Mustufa et al. | |
| 10,398,521 B2 | 9/2019 | Itkowitz et al. | |
| 2002/0093484 A1 | 7/2002 | Skala et al. | |
| 2002/0128552 A1 | 9/2002 | Nowlin et al. | |
| 2004/0015053 A1 | 1/2004 | Bieger et al. | |
| 2006/0241414 A1 | 10/2006 | Nowlin et al. | |
| 2007/0156126 A1 | 7/2007 | Flaherty | |
| 2009/0192524 A1 | 7/2009 | Itkowitz et al. | |
| 2009/0245600 A1 | 10/2009 | Hoffman et al. | |
| 2010/0082039 A1 | 4/2010 | Mohr et al. | |
| 2010/0161129 A1 | 6/2010 | Costa et al. | |
| 2010/0228265 A1 | 9/2010 | Prisco | |
| 2010/0331856 A1 | 12/2010 | Carlson et al. | |
| 2011/0230896 A1 | 9/2011 | Wallace et al. | |
| 2012/0320186 A1 | 12/2012 | Urban et al. | |
| 2013/0060278 A1 | 3/2013 | Bozung et al. | |
| 2013/0103197 A1 | 4/2013 | Mohr et al. | |
| 2013/0190776 A1 | 7/2013 | Zhang et al. | |
| 2013/0211588 A1 | 8/2013 | Diolaiti | |
| 2013/0304084 A1 | 11/2013 | Beira et al. | |
| 2013/0331644 A1 | 12/2013 | Pandya et al. | |
| 2014/0039521 A1 | 2/2014 | Mohr et al. | |
| 2014/0039681 A1 | 2/2014 | Bowling et al. | |
| 2014/0163359 A1 | 6/2014 | Sholev et al. | |
| 2014/0194896 A1 | 7/2014 | Frimer et al. | |
| 2014/0221738 A1 | 8/2014 | Sholev et al. | |
| 2014/0228632 A1 | 8/2014 | Sholev et al. | |
| 2014/0277747 A1 | 9/2014 | Walker et al. | |
| 2014/0323803 A1 | 10/2014 | Hoffman et al. | |
| 2015/0032126 A1 | 1/2015 | Nowlin et al. | |
| 2015/0051733 A1 | 2/2015 | Nowlin et al. | |
| 2016/0015473 A1 | 1/2016 | Frimer et al. | |
| 2016/0038011 A1 | 2/2016 | Diolaiti et al. | |
| 2016/0354166 A1 | 12/2016 | Popovic et al. | |
| 2017/0202629 A1 | 7/2017 | Maillet et al. | |
| 2017/0212723 A1 | 7/2017 | Atarot et al. | |
| 2019/0321117 A1 | 10/2019 | Itkowitz et al. | |

FOREIGN PATENT DOCUMENTS

| | | | | |
|---|---|---|---|---|
| JP | 2005261956 A | 9/2005 | | |
| JP | 2008228967 A | 10/2008 | | |
| KR | 20130092615 A | 8/2013 | | |
| KR | 20130121590 A | 11/2013 | | |
| WO | WO-2006124390 A2 | 11/2006 | | |
| WO | WO-2010039394 A1 | 4/2010 | | |
| WO | WO-2010117685 A2 | 10/2010 | | |
| WO | WO-2010151438 A1 | 12/2010 | | |
| WO | WO-2011060139 A2 | 5/2011 | | |
| WO | WO-2013027200 A2 | 2/2013 | | |
| WO | WO-2013027201 A2 | 2/2013 | | |
| WO | WO-2013027202 A2 | 2/2013 | | |
| WO | WO-2013122889 A1 | 8/2013 | | |
| WO | WO-2014024038 A1 | 2/2014 | | |
| WO | WO-2014151621 A1 * | 9/2014 | | A61B 17/32 |
| WO | WO-2015121765 A1 | 8/2015 | | |
| WO | WO-2015142953 A1 * | 9/2015 | | A61B 1/00009 |
| WO | WO-2016114090 A1 | 7/2016 | | |

OTHER PUBLICATIONS

Arkenbout et al, Robust hand motion tracking through data fusion of 5DT data glove and Nimble VR Kinect camera measurements, Sensors 2015, 15, 31644-31671; see attached NPL (Year: 2015).*
Extended European Search Report for Application No. EP21170697.3 mailed on Aug. 20, 2021, 8 pages.
Bajd T. et al., "Robotics" In: "Robotics", Jan. 15, 2010 (Jan. 15, 2010), Springer Netherlands, Dordrecht, XP055384691, ISBN: 978-90-48-13776-3, 1 page.
Burgner J., et al., "A Bimanual Teleoperated System for Endonasal Skull Base Surgery," IEEE/RSJ International Conference on Intelligent Robots and Systems(IROS), Sep. 2011, pp. 2517-2523.
Extended European Search Report for Application No. 15764617.5, mailed on Jul. 5, 2017, 9 pages.
Extended European Search Report for Application No. EP19191254.2, mailed on Oct. 24, 2019, 6 pages.
International Preliminary Report on Patentability for Application No. PCT/US2018/056874, mailed on May 7, 2020, 8 pages.
International Search Report and Written Opinion for Application No. PCT/US15/21105, mailed on Jun. 5, 2015, 11 pages.
International Search Report and Written Opinion for Application No. PCT/US2018/056874, mailed on Feb. 1, 2019, 10 pages.
King, B. W., et al., "Towards an Autonomous Robot for Camera Control during Laparoscopic Surgery," Journal of Laparoendoscopic & Advanced Surgical Techniques, vol. 23 (12), 2013, pp. 1027-1030.
Mudunuri, A. V., "Autonomous camera control system for surgical robots," Wayne State University Thesis, DigitalCommons, 2010, 87 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18871669.0 mailed on Nov. 12, 2020, 8 pages.
Extended European Search Report for Application No. EP23172384.2, mailed on Nov. 29, 2023, 09 pages.

* cited by examiner

SYSTEM AND METHOD FOR REPOSITIONING INPUT CONTROL DEVICES

RELATED APPLICATIONS

This patent application claims priority to and benefit of the filing date of U.S. Provisional Patent Application No. 62/577,020, entitled "System and Method for Repositioning Input Control Devices," filed Oct. 25, 2017, which is incorporated by reference herein in its entirety.

TECHNICAL FIELD

The present disclosure relates generally to teleoperation of devices with moveable arms and more particularly to repositioning input control devices.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more repositionable arms and/or end effectors. It is also common to operate the electronic devices via teleoperation using one or more input control devices on an operator workstation to control the motion and/or operation of the repositionable arms and/or the end effectors. When the electronic device is operated remotely from the operator workstation and/or the end effectors are being used in an area not directly visible to the operator, such as during computer-assisted surgery when the end effectors are hidden by patient anatomy, the electronic device may include an imaging device that captures a region of interest and displays it to the operator using a display system. To aid the operator in controlling the repositionable arms and/or the end effectors, it is helpful to maintain alignment between a position and/or orientation of each input control device used by the operator to manipulate an associated repositionable arm and/or end effector and the associated end effector. This provides the operator with an intuitive control over the associated end effector because relative motions of the input control device by the operator's hands are implemented as corresponding motion in the associated end effector as viewed using the imaging device. Thus, the associated end effector appears to follow the movements of the operator's hand.

Before alignment between the position and/or orientation of the input control device and the associated end effector is obtained, it is likely that the position and/or orientation of the input control device has to be changed (e.g., repositioned), without moving the associated end effector, to bring about the alignment between the position and/or orientation of the input control device and the position and/or orientation of the associated end effector. In addition, it may be helpful to periodically reposition the input control device while maintaining the alignment between the position and/or orientation of the input control device and the position and/or orientation of the associated end effector in order to place the input control device in a better ergonomic position for the operator. While it is possible for the repositioning of the input control device to be done manually by having the operator disengage the input control device from the associated end effector while the input control device is positioned and/or oriented to match the end effector as viewed using the imaging device. This, however, may be a tedious operation. Alternate approaches may include automated disengagement of the input control device from the associated end effector and automated repositioning. However, movement of the input control device that is not initiated by the operator may result in discomfort and/or injury to the operator.

Accordingly, improved methods and systems for repositioning input control devices are desirable.

SUMMARY

Consistent with some embodiments, an operator workstation for controlling a computer-assisted device includes an input control device for use by an operator, one or more sensors, and a controller coupled to the one or more sensors and the input control device. The controller is configured to determine whether the operator is interacting with the input control device using the one or more sensors and in response to determining a lack of operator interaction with the input control device, determine a trajectory for moving the input control device from a current position or orientation toward a desired position or orientation, and move the input control device along the trajectory.

Consistent with some embodiments, a method of controlling motion a computer-assisted device using a controller includes determining whether an operator is interacting with an input control device using one or more sensors and in response to detecting lack of operator interaction with the input control device, determining a trajectory for moving the input control device from a current position or orientation toward a desired position or orientation and moving, using one or more actuators, the input control device along the trajectory.

Consistent with some embodiments, a non-transitory machine-readable medium including a plurality of machine-readable instructions which when executed by one or more processors associated with an operator workstation are adapted to cause the one or more processors to perform a method that includes determining whether an operator is interacting with an input control device using one or more sensors and in response to detecting lack of operator interaction with the input control device, determining a trajectory for moving the input control device from a current position or orientation toward a desired position or orientation and moving, using one or more actuators, the input control device along the trajectory.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Figure 1:
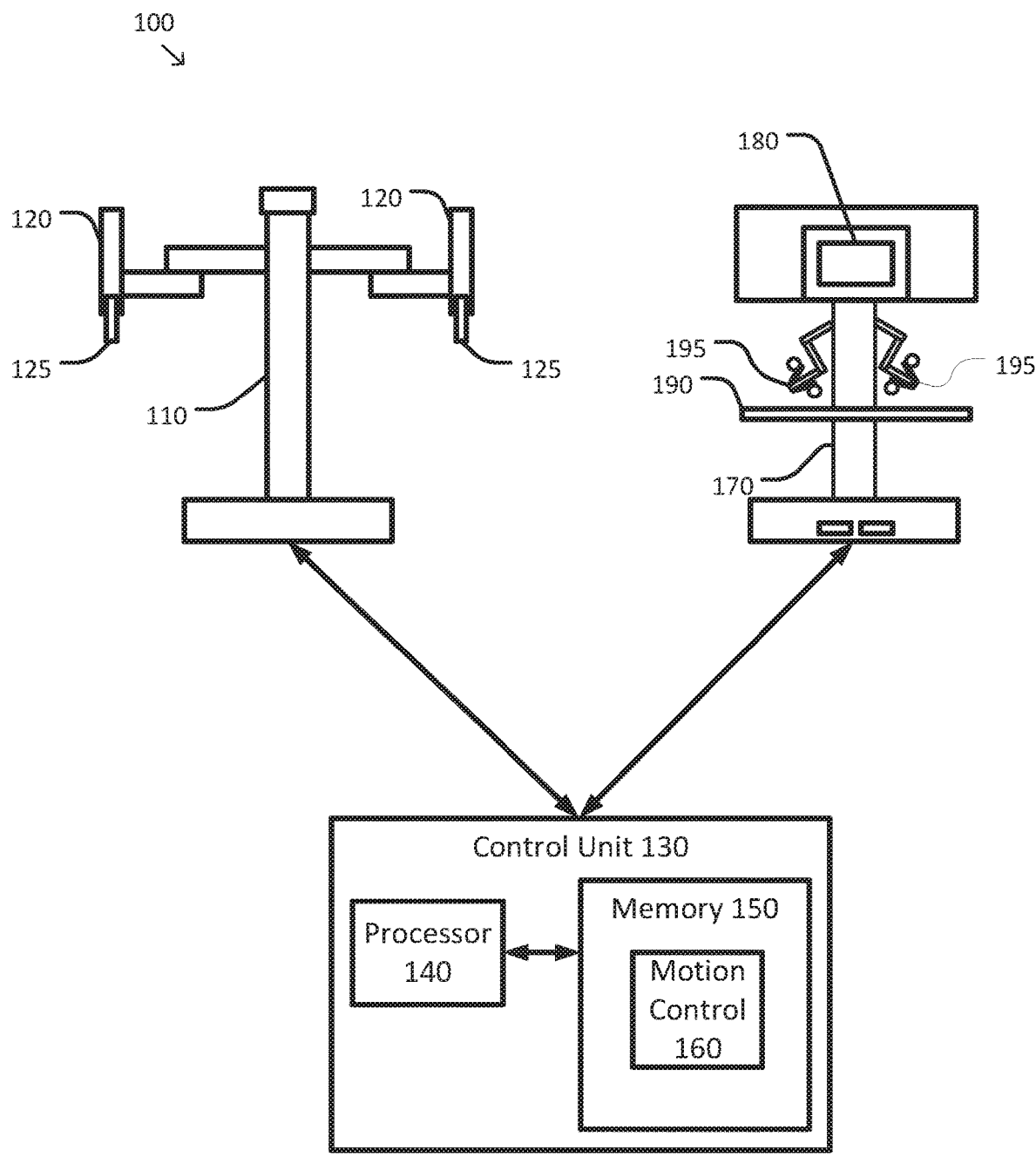
FIG. 1 is a simplified diagram of a computer-assisted system according to some embodiments.

In the figures, elements having the same designations have the same or similar functions.

DETAILED DESCRIPTION

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "shape" refers to a set positions or orientations measured along an object. As used herein, and for a device with repositionable arms, the term "proximal" refers to a direction toward the base of the device and "distal" refers to a direction away from the base.

Aspects of the invention are described primarily in terms of an implementation using a da Vinci® Surgical System (specifically, a Model IS4000, marketed as the da Vinci® Xi™ Surgical System), commercialized by Intuitive Surgical, Inc. of Sunnyvale, California Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000; the Model IS4200, commercialized as the da Vinci® X™ Surgical System) are merely exemplary and are not to be considered as limiting the scope of the inventive aspects disclosed herein. For example, any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

FIG. 1 is a simplified diagram of a computer-assisted system 100 according to some embodiments. As shown in FIG. 1, computer-assisted system 100 includes a device 110 with one or more movable or repositionable arms 120. Each of the one or more repositionable arms 120 may support one or more end effectors 125. In some examples, device 110 may be consistent with a computer-assisted surgical device. The one or more end effectors 125 may include instruments, imaging devices, and/or the like. In some medical examples, the instruments may include medical instruments, such as clamps, grippers, retractors, cautery tools, suction tools, suturing devices, and/or the like. In some medical examples, the imaging devices may include endoscopes, cameras, ultrasonic devices, fluoroscopic devices, and/or the like.

Device 110 is coupled to a control unit 130 via an interface. The interface may include one or more cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a motion control application 160 that may be used to support autonomous and/or semiautonomous control of device 110 as is described in further detail below.

Control unit 130 may further be coupled to an operator workstation 170 via the interface. Operator workstation 170 may be used by an operator, such as a surgeon, to control the movement and/or operation of the repositionable arms 120 and the end effectors 125. To support operation of the repositionable arms 120, operator workstation 170 includes a display system 180 for displaying images of at least portions of one or more of the repositionable arms 120 and/or end effectors 125. For example, display system 180 may be used when it is impractical and/or impossible for the operator to see the repositionable arms 120 and/or the end effectors 125 as they are being used. Operator workstation 170 may further include a console workspace with one or more input control devices 195 (sometimes called master control devices 195) that may be used for operating the device 110, the repositionable arms 120, and/or the end effectors 125. Each of the input control devices 195 may be coupled to the distal end of their own repositionable arms so that movements of the input control devices 195 may be detected by operator workstation 170 and communicated to control unit 130. To provide improved ergonomics, the console workspace may also include one or more rests, such as an arm rest 190 on which operators may rest their arms while manipulating the input control devices 195. In some examples, the display system 180 and the input control devices 195 may be used by the operator to teleoperate the repositionable arms 120 and/or the end effectors 125. In some embodiments, device 110, operator workstation 170, and control unit 130 may correspond to a da Vinci® Surgical System commercialized by Intuitive Surgical, Inc. of Sunnyvale, California.

In some embodiments, other configurations and/or architectures may be used with computer-assisted system 100. In some examples, control unit 130 may be included as part of operator workstation 170 and/or device 110. In some embodiments, computer-assisted system 100 may be found in an operating room and/or an interventional suite. And although computer-assisted system 100 includes only one device 110 with two repositionable arms 120, one of ordinary skill would understand that computer-assisted system 100 may include any number of devices with repositionable arms and/or end effectors of similar and/or different design from device 110. In some examples, each of the devices may include fewer or more repositionable arms 120 and/or end effectors 125. Additionally, although operator workstation 170 includes only two input control devices, one of ordinary skill would understand that operator workstation 170 may include any number of input control devices as well as other input devices, sensors, and/or the like.

Motion control application 160 may support autonomous and/or semiautonomous control of device 110 using operator workstation 170. Motion control application 160 may additionally include one or more application programming interfaces (APIs) for receiving position, motion, and/or other sensor information from device 110 and/or operator workstation 170, exchanging position, motion, and/or collision avoidance information with other control units regarding other devices, and/or planning and/or assisting in the planning of motion for device 110, repositionable arms 120, end effectors 125, input control devices 195, and/or the like. In addition, motion control application 160 may provide commands to one or more actuators used to control positions and/or orientations of repositionable arms 120, end effectors 125, input control devices 195, and/or the like. And although motion control application 160 is depicted as a software application, motion control application 160 may be implemented using hardware, software, and/or a combination of hardware and software.

One of the tasks of motion control application 160 is to establish and maintain an alignment between the position and/or orientation of each of the input control devices 195 and its associated end effector 125. This alignment may be established and maintained based on any appropriate reference or references appropriate to the system design. In some embodiments, the alignment of input control device 195 relative to its associated end effector 125 is determined based on the orientation of input control device 195 in an operator reference frame and the orientation of the associated end effector 125 in an imaging device reference frame; input control device 195 and its associated end effector 125 are considered to be aligned when their orientations are the same (or within a predetermined tolerance of each other) if the operator reference frame and imaging device reference frames are oriented in the same way. The operator reference frame may be defined by a part of the operator, something viewed by the operator, and/or the like. In some examples, the operator reference frame may be defined by the position and/or orientation of the operator's eyes, head, torso, etc. In some examples, the operator reference frame may be defined by the position and/or orientation of a head-mounted device, a viewer through which the operator looks through, a display configured to be viewed by the operator, and/or the like. In some examples, the imaging device reference frame may be defined by the tip of an imaging device, one or more imaging sensors of the imaging device, a field of view of the imaging device, and/or the like. In some medical examples, the imaging reference frame is defined by the field of view of an endoscope configured to capture images of the site of the medical procedure.

In some embodiments, several possible operational scenarios may result in the loss of alignment between the position and/or orientation of one of the input control devices 195 and the position and/or orientation of its associated end effector 125. In some examples, when an end effector 125 is mounted to a corresponding repositionable arm 120 (e.g., by connecting the repositionable arm 120 to a cannula used as a guide to insert end effector 125 into a patient and/or work space, connecting the repositionable arm 120 to a jig and/or other alignment device, and/or the like), repositioning of the input control device 195 associated with the mounted end effector 125 may occur to establish the alignment between the position and/or orientation of the input control device 195 and the position and/or orientation of the associated end effector 125. In some examples, when an input control device 195 is disassociated with a first end effector 125 and associated with a second end effector 125, repositioning of the input control device 195 to establish alignment between the position and/or orientation of the input control device 195 and the position and/or orientation of the second end effector 125 may occur to account for the differences in the position and/or orientation of the second end effector 125 relative to the imaging device and the position and/or orientation of the first end effector 125 relative to the imaging device. In some examples, other actions such as manual movement of a repositionable arm 120 and/or end effector 125 associated with input control device 195, repositioning of the imaging device used to view the one or more end effectors 125, movement of an input control device 195 that has been disengaged from an associated end effector 125, rearrangement of operator workstation (e.g., adjustment to arm rest 190), and/or the like may also result in having to reposition the one or more input control devices 195 to reestablish the alignment between the position and/or orientation of one or more input control devices 195 and the position and/or orientation of one or more associated end effectors 125.

In some examples, maintaining the alignment between the position and/or orientation of each of the input control devices 195 and the position and/or orientation of the associated end effectors 125 includes repositioning one or more of the input control devices 195 to position and/or orient the one or more of the input control devices 195 relative to an ergonomic center and/or default center position associated with the one or more of the input control devices 195. In some examples, the ergonomic center may set to a default, set as a preference by each operator, set according to a procedure being performed, adjusted as ergonomic features of operator workstation 170 (e.g., arm rest 190) are adjusted, learned by observing operation of operator workstation 170, and/or the like. Examples of techniques for learning an ergonomic center based on observation are described in International Patent Publication No. WO 2015/142953 (disclosing "System and Method for Recentering Imaging Devices and Input Controls"), which is hereby incorporated by reference in its entirety.

According to some embodiments, care should be exercised in automatically reestablishing the alignment between the position and/or orientation of the one or more input control device 195 and the position and/or orientation of the associated end effectors 125, as movement of the one or more input control devices 195 while the operator is still in contact with and/or trying to operate the one or more input control devices 195 may result in confusion, discomfort, and/or injury to the operator.

As is described in further detail below, computer-assisted system 100, motion control application 160, and operator workstation 170 are equipped with one or more features to allow motion control application 160 to detect when it is appropriate to reposition the one or more input control devices 195, plan appropriate repositioning trajectories, execute the planned trajectories, and terminate following of the planned trajectories when further repositioning is counter-indicated.

Figure 2:
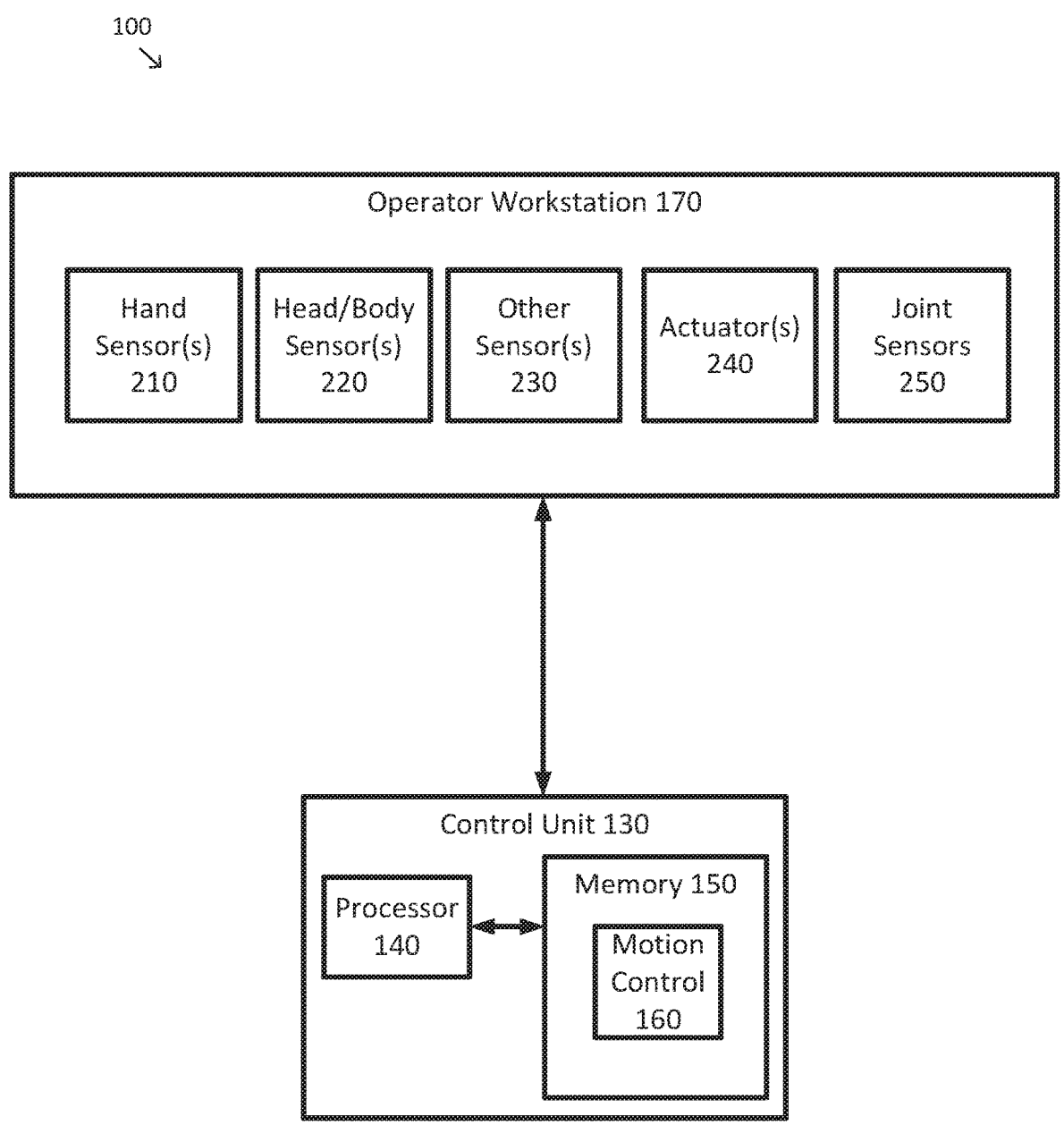
FIG. 2 is another simplified diagram of the computer-assisted system of FIG. 1 according to some embodiments.

FIG. 2 is another simplified diagram of computer-assisted system 100 according to some embodiments. More specifically, FIG. 2 shows the various sensors and actuators used by control unit 130 and motion control application 160 to manage and control the one or more input control devices 195 of operator workstation 170 to help establish and maintain the alignment between the position and/or orientation of the one or more input control device 195 and the position and/or orientation of the associated end effectors 125. One of ordinary skill would understand that the various sensors and/or actuators shown in FIG. 2 are representative only and that one or more of these sensors and/or actuators may be omitted, other sensors and/or actuators not shown may be present, and/or the like.

As shown in FIG. 2, operator workstation 170 may include any number and variety of sensors and actuators. That is, in various embodiments, operator workstation 170 may include no sensors, one sensor, or a plurality of sensors. And, in addition, operator workstation 170 may include no actuators, one actuator, or a plurality of actuators. In the specific example shown in FIG. 2, operator workstation 170 includes one or more hand and/or finger sensors 210 providing indications of operator interaction with the one or more input control devices. The one or more hand and/or finger sensors 210 may be used by motion control application 160 to determine whether a hand (or part of a hand such as a finger, or other body part) of the operator is in contact and/or in close proximity to one or more of the input control devices 195. In some examples, the one or more hand and/or finger sensors 210 may include one or more contact sensors, such as one or more: contact switches, capacitive touch sensors, pressure sensors, force sensors, and/or the like. In some examples, the one or more hand and/or finger sensors 210 may include one or more proximity sensors, such as one or more: infrared and/or ultrasonic ranging or proximity detectors, light walls, capacitive sensors, inductive sensors, RF sensors, optical sensors, imaging sensors, vision devices, and/or the like. In some examples, data from one or more contact or proximity sensors may be evaluated using one or more pattern and/or image processing techniques to differentiate the operator from other foreign objects in the vicinity of the input control device 195. In some examples, the one or more hand and/or finger sensors 210 may include the ability to detect motion, force, and/or torque applied by the operator to the one or more input control devices. In some examples, the one or more hand and/or finger sensors 210 may include the ability to determine contact or close proximity separately for each input control device 195 so that operator presence and/or interaction may be determined separately for each of the input control devices 195.

Operator workstation 170 further includes one or more head and/or body sensors 220 providing indications of operator interaction with the one or more input control devices. The one or more head and/or body sensors 220 may be used by motion control application 160 to determine whether an operator is present at operator workstation 170, in position at operator workstation 170 to operate operator workstation 170, in close proximity to operator workstation 170, and/or the like. In some examples, a head and/or body sensor 220 may be positioned to detect the head, neck, shoulders, torso, arms, waist, buttocks, legs, feet, or other body part of the operator. In some examples, the one or more head and/or body sensors 220 may include one or more contact sensors, such as one or more sensors utilizing the technologies listed above for hand and/or finger sensors, and/or the like to determine whether the head of the operator is in a position to view images displayed on display system (e.g., to view the one or more end effectors 125 in images captured by the imaging device, to view stereoscopic images, and/or the like), to determine whether the operator is in contact or close proximity to other portions of operator workstation 170 (e.g., arm rest 190, a seat, and/or the like), and/or the like. In some examples, the one or more head and/or body sensors 220 may include one or more proximity sensors, such as one or more sensors utilizing the technologies listed above for hand and/or finger sensors, gaze trackers, and/or the like to detect the head and/or body of the operator in close proximity to operator workstation 170. In some examples, data from the one or more proximity sensors may be evaluated using one or more pattern and/or image processing techniques to differentiate the operator from other foreign objects in the vicinity of the input control device 195.

Operator workstation 170 further includes one or more other sensors 230 providing indications of operator interaction with the one or more input control devices. The one or more other sensors 230 may include one or more other controls and/or input devices of operator workstation 170, used by the operator to control operation of computer-assisted device 110, that may be separate from the one or more input control devices 195 whose position and/or orientation is being kept in alignment with the position and/or orientation of the associated one or more end effectors 125. In some examples, the one or more other sensors may include one or more foot pedals, switches, buttons, knee levers, and/or the like. In some examples, the one or more other sensors 230 may include one or more motion sensors for determining whether there is movement in the one or more input control devices.

In some embodiments, the operator workstation 170 further includes one or more actuators 240 for controlling the position and/or orientation of the one or more input control devices 195. In some examples, the one or more actuators 240 may include one or more rotational or linear motors, servos, and/or the like used to control the positions and/or orientations of joints in the one or more input control devices 195. In some examples, operator workstation 170 may further include one or more joint sensors 250 for measuring position, orientation, velocity, rotational velocity, force, and/or torque within the joints of the one or more input control devices 195 so as to support closed-loop control of the one or more input control devices 195, the ability to measure position errors of the one or more input controls devices 195, applied forces and/or torques on the one or more input control devices 195, and/or the like.

In some examples, some sensors may serve multiple purposes. For example, one of the joint sensors 250 that is used to provide information for a feedback control system for an input control device may also be used to provide information for determining whether the operator is interacting with the input control device. In some examples, motion of a joint detected by one of the joint sensors 250 may be used by the feedback control system in a control loop, as well as used in a determination that operator interaction is causing the motion of the joint.

Figure 3:
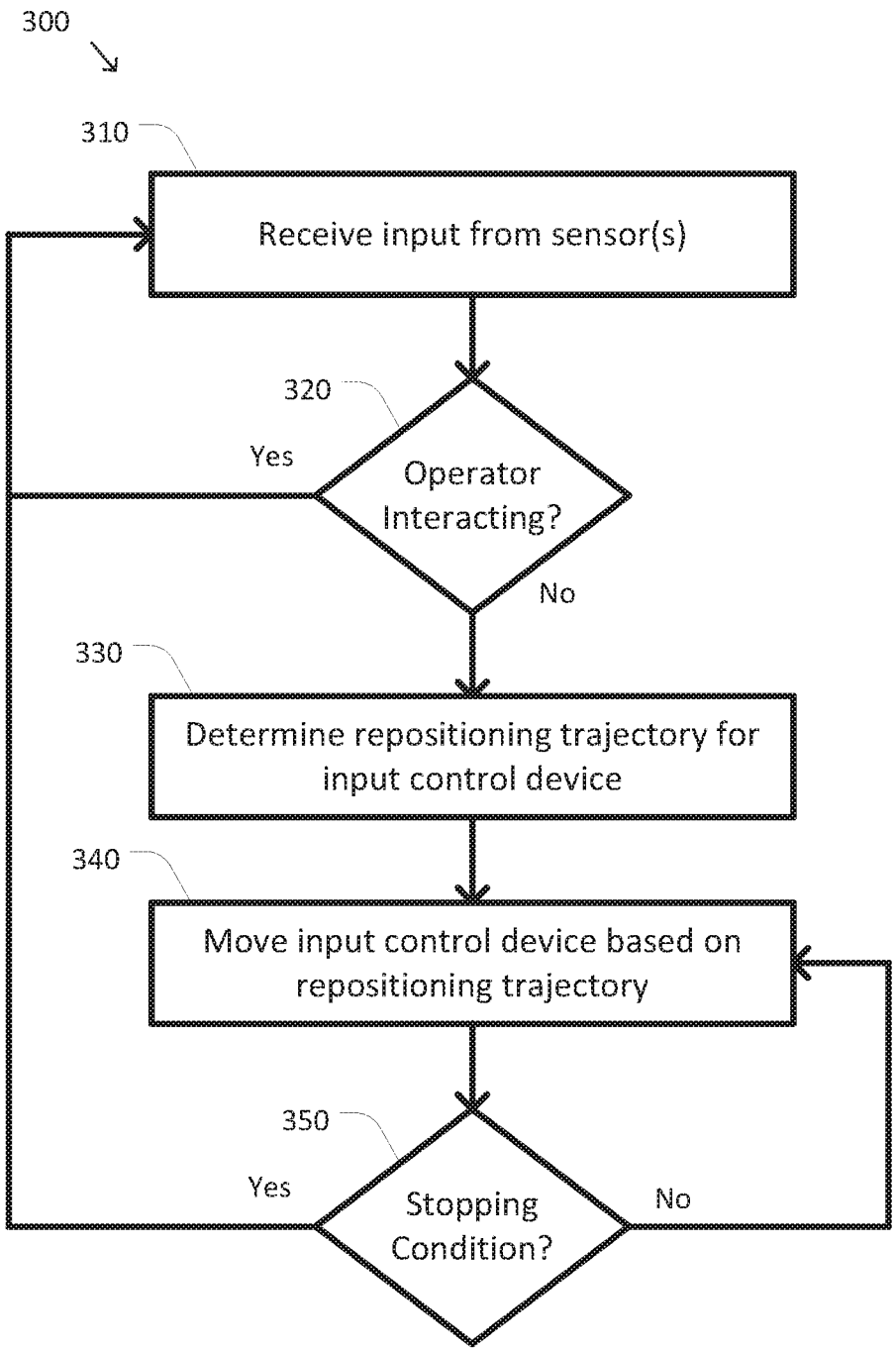
FIG. 3 is a simplified diagram of a method of repositioning input control devices according to some embodiments.

FIG. 3 is a simplified diagram of a method 300 of repositioning input control devices according to some embodiments. One or more of the processes 310-350 of method 300 may be implemented, at least in part, in the form of executable code stored on non-transitory, tangible, machine-readable media that when run by one or more processors (e.g., the processor 140 in control unit 130) may cause the one or more processors to perform one or more of the processes 310-350. In some embodiments, method 300 may be performed by an application, such as motion control application 160. In some embodiments, method 300 may be used to reposition one or more input control devices, such as the one or more input control devices 195, so that the position and/or orientation of the each of the input control devices is kept in alignment with the position and/or orientation of an associated end effector, such as the one or more end effectors 125. In some embodiments, method 300 delays repositioning of the input control devices until it is determined that an operator is not interacting with the input control devices in order to reduce the likelihood of discomfort and/or injury to the operator caused by the repositioning of the input control devices.

According to some embodiments, the processes of method 300 may be applied independently for each input control device, in synchronization with the other input control devices (i.e., so that repositioning movements occur concurrently for each input control device that is being repositioned), and/or all together so that repositioning of one of the input control devices is not performed unless all of the input control devices are free to be repositioned. In some embodiments, one or more of the processes of method 300 may be performed in a different order than the order implied by the flow chart in FIG. 3. In some examples, the sensor reading of process 310 and the tests of process 320 may be performed as part of process 350. In some examples, process 330 may be performed periodically with the repetition of processes 340 and 350 to allow for redetermination of the repositioning trajectory while a previously determined repositioning trajectory is being applied to the input control devices. In some embodiments, processes 340 and 350 may be omitted when there is no repositioning move to perform. In some embodiments, process 330 may occur before and/or or concurrently with processes 310 and/or 320 so that the repositioning trajectory is being computed as the input control device is manipulated by the operator.

At a process 310, input is received from one or more sensors. In some examples, the one or more sensors include one or more hand and/or finger sensors or other sensors for operator detection, such as the one or more hand and/or finger sensors 210. In some examples, the one or more sensors may include sensors used for feedback control, such as joint sensors like the one or more joint sensors 250. Each of the one or more hand and/or finger sensors may provide an indication of whether an operator's hand is in contact with and/or close proximity to each of the input control devices. In some examples, each of the one or more hand and/or finger sensors may provide a binary indication (e.g., either: (a) a hand is in contact with or near an input control device or (b) a hand is not in contact with or near an input control device), an analog indication (e.g., how close the hand is to the input control device, or where the hand is relative to the input control device), and/or a certainty level of whether a hand is in contact with or near an input control device. In some examples, evaluation of the input from the one or more hand and/or finger sensors may include performing one or more pattern and/or image processing techniques to make the binary, analog, and/or certainty level determination. In some examples, the one or more hand and/or finger sensors are able to indicate whether a hand is in contact with or near an input control device separately for each of the input control devices and/or when a hand is in contact with or near any of the input control devices.

In some examples, the one or more operator detection sensors include one or more head and/or body sensors, such as the one or more head and/or body sensors 220. Each of the one or more head and/or body sensors may provide an indication of whether an operator is at or near the operator workstation. In some examples, each of the one or more head and/or body sensors may provide a binary indication (e.g., either: (a) an operator is at or near the operator workstation or (b) an operator is not at or near the operator workstation), an analog indication (e.g., how close the operator is to the operator workstation, or where the operator is relative to the operator workstation), and/or a certainty level of whether the operator is at or near the operator workstation. In some examples, evaluation of the input from the one or more head and/or body sensors may include performing one or more pattern and/or image processing techniques to make the binary, analog, and/or certainty level determination.

In some examples, the one or more operator detection sensors include one or more other sensors, such as the one or more other sensors 230. The one or more other sensors may provide a secondary and/or alternate means for determining whether the operator is present at the operator workstation and/or likely to interact with the input controls.

At a process 320, a determination is made as to whether the operator is interacting with one or more of the input control devices based on the input received during process 310 from the one or more operator detection sensors. In some examples, the determination as to whether the operator is interacting with an input control device may be made individually for each of the input control devices and/or jointly for the input control devices collectively (i.e., a determination of interaction with one of the input control devices results in a determination of interaction with all of the input control devices). In some examples, a determination that the operator is interacting with an input control device may be made in response to any one of the operator detection sensors providing a positive indication that the operator is interacting with the input control device (e.g., a positive indication from any one of the hand, head, body, and/or other sensors indicates operator presence, proximity, and/or interaction). In some examples, a determination that the operator is interacting with an input control device may be made in response to all of the operator detection sensors providing a positive indication of operator presence, proximity, and/or interaction. In some examples, a voting and/or weighted sum combination of input from each of the one or more operator detection sensors may be used to determine whether the operator is interacting with the input control device. In some examples, the voting strength and or weights may vary among the one or more operator detection sensors. In some examples, a greater weight or vote is assigned to the one or more hand and/or finger sensors, a lower weight or vote is assigned to the one or more head and/or body sensors, and/or a lowest weight or vote is assigned to the one or more other sensors. In some examples, detection of operator interaction by one of the operator detection sensors (e.g., one of the hand and/or finger sensors) may override a detection of lack of interaction by any other of the operator detection sensors including one of the sensors at the input control device and/or the workstation.

According to some embodiments, a determination of lack of interaction by the operator with an input control device may include determining that lack of interaction by the operator has occurred for a predetermined minimum duration. In some examples, the predetermined minimum duration may be configurable based on operator preferences, a procedure being performed, and/or the like. In some examples, the predetermined minimum duration may be in a range from 5 seconds to 60 seconds or more.

When a determination is made that the operator is interacting with an input control device, the input control device is further monitored for interaction by returning to process 310. When a determination is made that the operator is not interacting with an input control device a repositioning move for the input control device may be made beginning with process 330.

At the process 330, a repositioning trajectory for the input control device is determined for the input control device for which a determination of non-interaction by the operator was determined during process 320. In some embodiments, when non-interaction is determined for more than one input control device during process 320, a repositioning trajectory is determined for each of the input control devices. Determining the repositioning trajectory for an input control device includes generating a motion plan that repositions the input control device from its current position and/or orientation to a desired position and/or orientation. In some examples, the desired position and/or orientation may be associated with a position and/or orientation to reestablish alignment between the position and/or orientation of the input control device and its associated end effector. In some examples, the desired position and/or orientation may be associated with a position and/or orientation to reposition the input control device about an ergonomic center, a default input control device center, and/or the like of the operator workstation. In some examples, the repositioning trajectory includes a change in position of a distal end of the input control device, a change in orientation of the distal end of the input control device, or both a change in the position and orientation of the distal end of the input control device. In some examples, the repositioning trajectory may include linearly translating the distal end of the input control device from its current position to the desired end position along a linear path. In some examples, the repositioning trajectory is determined based on inverse kinematics and/or a Jacobian transpose of the input control device.

According to some embodiments, the repositioning trajectory may be constrained by one or more factors. In some examples, the speed (i.e. magnitude of the velocity) of the repositioning move (e.g., the speed of the distal end of the input control device) may be kept below a threshold speed. In some examples, the threshold speed may be selected from a range from 0.1 to 1.0 centimeters per second. In some examples, the threshold speed may be set based on operator preference, a procedure being performed, a type and/or configuration of the operator workstation, an amount of time elapsed since the operator's last interaction, and/or the like. In some examples, the threshold speed may be set based on a distance between the current position of the distal end of the input control device and the desired position of the distal end of the input control device (e.g., a length of the repositioning trajectory). In some examples, the threshold speed may be proportional to the distance between the current position of the distal end of the input control device and the desired position of the distal end of the input control device so that longer repositioning trajectories occur with a higher threshold speed. In some examples, the threshold speed may be set based on the results of the voting and/or weighted sum determined during process 320 so that a weaker or lower strength indication of lack of operator interaction results in a lower threshold speed. For example, when lack of operator interaction with the input control device is determined based on input received from the one or more hand and/or finger sensors, but operator presence is determined based on input from the one or more head, body, and/or other sensors, a lower threshold speed would be set than if lack of operator presence is also determined based on input from the one or more head, body, and/or other sensors. In some examples, the repositioning trajectory may include a startup delay of 5 seconds to 60 seconds or more before actual repositioning motion begins.

According to some embodiments, the repositioning trajectory may be coordinated with the repositioning trajectory of another input control device that is also being repositioned. In some examples, the repositioning trajectory for each of the input control devices being repositioned may be coordinated so that each repositioning trajectory starts and stops at approximately the same time. In some examples, the repositioning trajectory may be implemented to avoid collisions with other input control devices, collisions with other parts of the operator workstation, range of motion limits of one or more joints of the input control device, collisions with the operator (e.g., known or expected locations of a knee, an alternate hand, and/or other body parts), and/or the like.

At a process 340, the input control device is moved based on the repositioning trajectory determined during process 330. In some examples, the movement may be accomplished by sending one or more commands to the one or more actuators, such as the one or more actuators 240, used to actuate the input control device. In some examples, the one or more commands may include sending one or more currents, voltages, pulse-width modulated signals, and/or the like to the one or more actuators. In some examples, the movement may be operated under closed-loop control using one or more joint sensors, such as the one or more joint sensors 250. In some examples, the movement may be made subject to one or more speed limits (e.g., the threshold speed), torque limits, and/or the like.

At a process 350, it is determined whether a stopping condition for the repositioning trajectory implemented during process 340 is detected. In some examples, the stopping condition may correspond to the input control device reaching the desired position and/or orientation (e.g., due to a successfully completed repositioning of the input control device). In some examples, the stopping condition may correspond to determining that the operator is now interacting with the input control device, such as by using processes similar to processes 310 and 320. In some examples, the thresholds, weights, and/or the like used by process 350 may be the same or different from those used for processes 310 and 320.

In some examples, the stopping condition may correspond to detecting that the input control device is having difficulty following the repositioning trajectory, such as may be due to a collision of the input control device with an obstacle, otherwise undetected attempts by the operator to resist the repositioning movement, and/or the like. In some examples, detecting the difficulty in following the repositioning trajectory may include detecting that a magnitude of a force or torque and/or a magnitude of a derivative of the force and/or torque applied by one of the actuators implementing the repositioning trajectory exceeds a configurable magnitude limit, a magnitude of a position error above a corresponding configurable magnitude threshold for a joint of the input control device and/or for the distal end of the input control device, a speed of a joint of the input control device and/or the distal end of the input control device above or below corresponding configurable speed thresholds, and/or the like. In some examples, the magnitude of the force, torque, position, and/or speed may be determined using the one or more joint sensors. In some examples, the derivatives may be determined using a numerical differentiation technique, such as by using finite differences.

In some examples, detecting the difficulty in following the repositioning trajectory may include detecting that a magnitude of an aggregation of forces and/or torques applied by corresponding actuators is above a configurable aggregate force and/or torque magnitude threshold, a derivative of the aggregation of the forces and/or torques is above a configurable aggregate change in force and/or torque magnitude threshold, an aggregation of changes in currents of corresponding actuators is above an aggregate current change magnitude threshold, an aggregation of position errors and/or change in position errors for joints of the input control device is above or below configurable aggregate position and/or configurable aggregate speed threshold, and/or the like. In some examples, the aggregations may be determined according to an average, a weighted sum, and/or the like.

In some examples, a stopping condition may not be detected unless it is determined that the magnitude of the position error, speed, force, torque, derivative of force, and/or derivative of speed is outside an acceptable range for a configurable threshold period of time.

In some examples, the stopping condition may correspond to a change in system state of the computer-assisted device and/or the operator workstation, such as attachment or removal of an end effector from the computer-assisted device, repositioning of the imaging device, actuation of a state change by the operator, activation of a clutch and/or other motion interrupting input, detection of an error condition, and/or the like.

According to some embodiments, the determination of a stopping condition may be separate for each input control device or determined in coordination with stopping conditions for each of the input control devices. In some examples, the stopping condition may be detected separately for each of the input control devices with detection of a stopping condition for one input control device affecting just the repositioning movement for that input control device. In some examples, the detection of a stopping condition for any of the input control devices is a stopping condition for each of the input control devices and is used to abort repositioning movement for each of the input control devices.

When a stopping condition is detected, method 300 returns to process 310 to receive additional input from the one or more operator detection sensors and re-determine whether the operator is interacting with one or more of the input control devices. When a stopping condition is not detected, method 300 returns to process 340 to continue moving the input control device based on the repositioning trajectory.

Some examples of control units, such as control unit 130 may include non-transitory, tangible, machine readable media that include executable code that when run by one or more processors (e.g., processor 140) may cause the one or more processors to perform the processes of method 300. Some common forms of machine readable media that may include the processes of method 300 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. An operator workstation for controlling a computer-assisted device, the operator workstation comprising:
   an input control device configured to be used by an operator to teleoperate an end effector where motions of the input control device specify corresponding motions of the end effector;
   a plurality of contact or proximity sensors included on the operator workstation that detect whether the input control device is receiving interactions from one or more body parts of the operator; and
   a controller coupled to the plurality of contact or proximity sensors and the input control device, the controller being configured to:
   determine that the input control device has not received any operator interactions specifying corresponding motions of the end effector for a threshold amount of time based on a weighted combination of a plurality of indications of operator interaction with the input control device, wherein each of the plurality of indications is provided by a different sensor included in the plurality of contact or proximity sensors; and
   in response to determining that the input control device has not received the operator interactions specifying corresponding motions of the end effector for the threshold amount of time:
      determine a trajectory for moving the input control device from a current position or orientation toward a desired position or orientation; and
      move the input control device along the trajectory.

2. The operator workstation of claim 1, wherein, to determine the trajectory for moving the input control device from the current position or orientation toward the desired position or orientation, the controller is configured to:
   determine the trajectory for moving the input control device from the current position toward the desired position.

3. The operator workstation of claim 1, wherein, to determine the trajectory for moving the input control device from the current position or orientation toward the desired position or orientation, the controller is configured to:
   determine the trajectory for moving the input control device from the current position and orientation toward the desired position and orientation.

4. The operator workstation of claim 1, wherein the controller is further configured to stop movement of the input control device along the trajectory in response to detecting a stopping condition.

5. The operator workstation of claim 4, wherein the stopping condition comprises:
   detecting a change in state of the operator workstation or the computer-assisted device, or
   detecting operator interaction with the input control device, or
   detecting difficulty in moving the input control device along the trajectory.

6. The operator workstation of claim 4, wherein the stopping condition comprises detecting operator interaction with another input control device.

7. The operator workstation of claim 1, wherein:
   the operator interaction with the input control device comprises the operator manipulating the input control device using a hand;
   the plurality of contact or proximity sensors include at least one head sensor and at least one body sensor; and
   to determine whether the operator is interacting with the input control device using the plurality of contact or proximity sensors, the controller is configured to use input from the at least one head sensor and the at least one body sensor to determine whether the operator is present at the operator workstation.

8. The operator workstation of claim 1, wherein the weighted combination includes a first weight for a hand or finger sensor of the plurality of contact or proximity sensors and a second weight for a head or body sensor of the plurality of contact or proximity sensors, and wherein the first weight is higher than the second weight.

9. The operator workstation of claim 1, wherein:
   the controller is further configured to determine whether the operator is interacting with the input control device based on a combination of separate indications of interaction, each of the separate indications of interaction being from a corresponding one of the plurality of contact or proximity sensors; and
   an indication of interaction by a first sensor of the plurality of contact or proximity sensors overrides an indication of lack of interaction by a second sensor of the plurality of contact or proximity sensors.

10. The operator workstation of claim 1, wherein to determine that the input control device has not received the operator interactions specifying corresponding motions of the end effector for the threshold amount of time, the controller is configured to determine a lack of operator interaction with another input control device.

11. The operator workstation of claim 1, wherein to determine that the input control device has not received the operator interactions specifying corresponding motions of the end effector for the threshold amount of time, the controller is configured to determine a lack of operator interaction with the input control device independently of determining a lack of operator interaction with one or more other input control devices.

12. The operator workstation of claim 1, wherein a speed of the trajectory is determined based on a length of the trajectory.

13. The operator workstation of claim 1, wherein a speed of the trajectory is kept below a maximum speed.

14. The operator workstation of claim 1, wherein the trajectory maintains an orientation of the input control device based on an orientation of the end effector.

15. The operator workstation of claim 1, wherein the desired position or orientation is based on a position or orientation of the end effector.

16. The operator workstation of claim 1, wherein the desired position or orientation is based on an ergonomic or other center of the operator workstation, or based on an ergonomics setting associated with the operator workstation.

17. The operator workstation of claim 1, wherein the desired position or orientation is based on a size of the operator.

18. The operator workstation of claim 1, wherein the computer-assisted device is a medical device comprising a manipulator for supporting a medical instrument, and wherein the controller is further configured to control the medical instrument based on input received from the input control device.

19. A method of controlling motion of a computer-assisted device, the method comprising:
- determining, by a controller, that an input control device of an operator workstation has not received any operator interactions specifying corresponding motions of an end effector for a threshold amount of time based on a weighted combination of a plurality of indications of operator interaction with the input control device, the input control device configured to be used by an operator to teleoperate the end effector where motions of the input control device specify corresponding motions of the end effector, wherein each of the plurality of indications is provided by a different sensor included in a plurality of contact or proximity sensors included on the operator workstation that detect whether the input control device is receiving interactions from one or more body parts of the operator; and
- in response to determining, by the controller, the input control device has not received the operator interactions specifying corresponding motions of the end effector for the threshold amount of time:
  - determining, by the controller, a trajectory for moving the input control device from a current position or orientation to a desired position or orientation; and
  - moving, by the controller using one or more actuators, the input control device along the trajectory.

20. The method of claim 19, wherein determining the trajectory for moving the input control device from the current position or orientation toward the desired position or orientation comprises determining the trajectory for moving the input control device from the current position and orientation toward the desired position and orientation.

21. The method of claim 19, further comprising stopping movement of the input control device along the trajectory in response to detecting one or more of:
- a change in state of the operator workstation or the computer-assisted device;
- operator interaction with the input control device;
- operator interaction with another input control device; or
- difficulty in moving the input control device along the trajectory.

22. The method of claim 19, wherein within the weighted combination, an indication of interaction by a first sensor of the plurality of contact or proximity sensors overrides an indication of lack of interaction by a second sensor of the plurality of contact or proximity sensors.

23. The method of claim 19, wherein the trajectory maintains an orientation of the input control device based on an orientation of the end effector.

24. A non-transitory machine-readable medium comprising a plurality of machine-readable instructions which when executed by one or more processors associated with an operator workstation are adapted to cause the one or more processors to perform a method comprising:
- determining that an input control device of the operator workstation has not received any operator interactions specifying corresponding motions of an end effector for a threshold amount of time based on a weighted combination of a plurality of indications of operator interaction with the input control device, the input control device configured to be used by an operator to teleoperate the end effector where motions of the input control device specify corresponding motions of the end effector, wherein each of the plurality of indications is provided by a different sensor included in a plurality of contact or proximity sensors included on the operator workstation that detect whether the input control device is receiving interactions from one or more body parts of the operator; and
- in response to determining the input control device has not received the operator interactions specifying corresponding motions of the end effector for the threshold amount of time:
  - determining a trajectory for moving the input control device from a current position or orientation to a desired position or orientation; and
  - moving, using one or more actuators, the input control device along the trajectory.

25. The non-transitory machine-readable medium of claim 24, wherein the method further comprises stopping movement of the input control device along the trajectory in response to one or more of:
- detecting a change in state of the operator workstation or a computer-assisted device controlled by the operator workstation;
- detecting operator interaction with the input control device;
- detecting operator interaction with another input control device; or
- detecting difficulty in moving the input control device along the trajectory.

26. The non-transitory machine-readable medium of claim 24,
wherein within the weighted combination, an indication of interaction by a first sensor of the plurality of contact or proximity sensors overrides an indication of lack of interaction by a second sensor of the plurality of contact or proximity sensors.

27. The non-transitory machine-readable medium of claim 24, wherein the trajectory maintains an orientation of the input control device based on an orientation of the end effector.

* * * * *